United States Patent [19]

Barnett et al.

[11] 4,211,870

[45] Jul. 8, 1980

[54] PREPARATION OF SUBSTITUTED 2-AMINOPYRAZINES

[75] Inventors: Charles J. Barnett, Indianapolis; Thomas L. Emmick, Greenfield; Richard C. Hoying, Indianapolis, all of Ind.

[73] Assignee: Eli Lilly and Company, Indianapolis, Ind.

[21] Appl. No.: 27,630

[22] Filed: Apr. 6, 1979

[51] Int. Cl.$^2$ .......................................... C07D 241/20
[52] U.S. Cl. ................................... 544/336; 424/250
[58] Field of Search .......................................... 544/336

[56] References Cited

PUBLICATIONS

Sharp et al., J. Chem. Soc. 932 (1951).
Taylor et al., J. Am. Chem. Soc. 90, 2424, (1968).
Taylor et al., J. Am. Chem. Soc. 95, 6407–6412, (1973).
Lang et al., Tetrahedron Letters 3967–3970, (1974).
Masaki et al., Bull. Chem. Soc. Japan 36, 922 (1963).
Masaki et al., J. Org. Chem. 29, 3165, (1964).
Masaki et al., Bull. Chem. Soc. Japan 39, 2745 (1966).

*Primary Examiner*—Jose Tovar
*Attorney, Agent, or Firm*—Leroy Whitaker; Dwight E. Morrison; Arthur R. Whale

[57] ABSTRACT

Preparation of substituted 2-aminopyrazines by reaction of an α-chloro or α-bromo oxime with an aminoacetonitrile in the presence of an acid-uptake agent, followed by separation of the intermediate novel hydroxyimino-substituted aminoacetonitrile, and cyclization thereof with acid.

12 Claims, No Drawings

PREPARATION OF SUBSTITUTED 2-AMINOPYRAZINES

BACKGROUND OF THE INVENTION

1. Field of the Invention

This invention relates to a method of heterocyclic synthesis, and in particular to a novel process for the preparation of substituted 2-aminopyrazine compounds, useful as intermediates in the preparation of insecticidal benzoylpyrazinylureas disclosed and claimed in Belgian Pat. No. 833288 (Mar. 11, 1976).

2. Description of the Prior Art

One of the main methods of synthesizing pyrazine compounds is by building up the pyrazine ring system from aliphatic components, and the essential step in most pyrazine syntheses from aliphatic components is formation of carbon-nitrogen bonds. Starting materials utilized can include $\alpha,\beta$-dicarbonyl compounds, $\alpha$-aminocarbonyl compounds, $\alpha$-aminonitriles, and $\alpha$-halogenoketones.

In the prior art, Sharp et al., *J. Chem. Soc.* 932 (1951), describe the condensation of $\alpha$-aminonitriles with oximinomethyl ketones to yield 3,5-disubstituted 2-aminopyrazine-1-oxides, which are then heated with sodium hydrosulphite to reduce the oxides to yield 3,5-disubstituted 2-aminopyrazines. This reference teaches that the efficiency of the general reaction is decreased by the replacement of alkyl with aryl groups.

In another reference, Taylor et al., *J. Am. Chem. Soc.* 95, 6407–6412 (1973), describe the preparation of 2-amino-3-carbamoyl-5-substituted-pyrazine-1-oxides, from the condensation of $\alpha$-aminocyanoacetamide with an oximinoketone, for example, oximinoacetophenone or oximinoacetone, in glacial acetic acid solution. The products are used in pteridine syntheses.

Taylor et al., *J. Am. Chem. Soc.*, 90, 2424 (1968), also describe the preparation of 2-amino-3-carbethoxy-5-methylpyrazine-1-oxide by the condensation of ethyl $\alpha$-aminocyanoacetate with isonitrosoacetone (oximinoacetone) in glacial acetic acid. The product is also used in the synthesis of pteridines.

Yet another prior art reference is Lang et al., *Tetrahedron Letters* 3967–3970 (1974), which discloses a synthesis of aminopyrazines by condensation of the tosylate of the isonitroso derivative of malononitrile, or cyanoacetic ester, with a substituted enamine, followed by reaction of the condensation product with ammonia to yield the 2-amino-3,5,6-trisubstituted pyrazine. The products are alleged by Lang et al. to possess tuberculostatic and diuretic properties.

Also in the prior art is Masaki et al., *Bull. Chem. Soc. Japan*, 36, 922 (1963), which discloses the reaction of $\alpha$-halo oximes with amines. The product thereby obtained is reductively cyclized using Raney nickel catalyst to yield a piperazinone.

Also included in the prior art are Masaki et al., *J. Org. Chem.* 29, 3165 (1964), and Masaki et al., *J. Org. Chem.* 31, 4143 (1966), both of which references disclose the reaction of protected $\alpha$-aminohydroxamic acid with an $\alpha$-chloro oxime, followed by removal of the oxime and O-benzyl groups, and treatment with ammonia to yield aspergillic acid-type compounds.

Another prior art reference is that of Masaki et al., *Bull. Chem. Soc. Japan*, 39, 2745 (1966), which teaches, inter alia, that the reaction of 1-chloro-2-oximino-3-butanone with aminoacetonitrile yields a mixture of N-(2-oximino-3-oxobutyl)aminoacetonitrile and N,N-bis(2-oximino-3-oxobutyl)aminoacetonitrile. These compounds were confirmed as the corresponding amidoxime and benzoyl or p-nitrobenzoyl derivatives, respectively. Ring closure of N-(2-oximino-3-oxobutyl)aminoacetonitrile by treatment with acids or by conversion of the nitrile into the iminoether was attempted, but the corresponding cyclic compound was not isolated.

SUMMARY OF THE INVENTION

This invention relates to a novel method of preparing substituted 2-aminopyrazines by reaction of an $\alpha$-chloro or $\alpha$-bromo oxime with an aminoacetonitrile, in the presence of an acid-uptake agent, followed by separation of the intermediate novel hydroxyimino-substituted amino-acetonitriles and cyclization thereof with acid.

DESCRIPTION OF THE PREFERRED EMBODIMENTS

This invention relates to a novel method for the preparation of 2-aminopyrazines of the formula

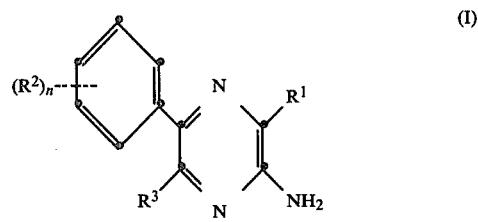

(I)

wherein
$R^1$ is hydrogen or $C_1$–$C_4$ alkyl;
$R^2$ is hydrogen, halo, $C_1$–$C_3$ alkyl, or trifluoromethyl;
n is 0, 1, or 2, with the proviso that when n=2, only one ortho position may be substituted; and
$R^3$ is $C_1$–$C_4$ alkyl, which comprises (A) reacting an aminoacetonitrile of the formula

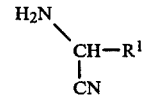

wherein $R^1$ has the same value as set forth hereinbefore, with an $\alpha$-chloro or $\alpha$-bromo oxime of the formula

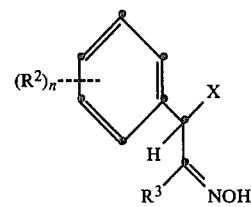

wherein X is chloro or bromo, and $R^2$, $R^3$, and n have the same values as set forth hereinbefore, in a solvent in the presence of an acid-uptake agent, to yield a hydroxyimino-substituted aminoacetonitrile of the following formula (II)

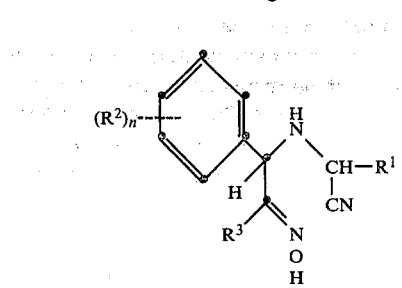

(II)

wherein $R^1$, $R^2$, $R^3$, and n have the same values as set forth hereinbefore; (B), separating the hydroxyimino-substituted aminoacetonitrile; and (C), heating the thus obtained hydroxyimino-substituted aminoacetonitrile with an acid selected from the group consisting of polyphosphoric acid, 85% phosphoric acid, and a mixture of phosphoric acid with phosphorus pentoxide, at a temperature of from about 50° to about 140° C., for from about ½ to about 4 hours, and isolating the product.

The hydroxyimino-substituted aminoacetonitriles of formula (II), above, are claimed in U.S. application Ser. No. 27,627, filed of even date with the present application.

In the above formulae, $C_1$-$C_3$ alkyl represents methyl, ethyl, n-propyl, or isopropyl.

Also in the above formulae, $C_1$-$C_4$ alkyl represents methyl, ethyl, n-propyl, isopropyl, n-butyl, sec.-butyl, t-butyl, or isobutyl.

Halo represents bromo, chloro, fluoro, or iodo.

The novel method of this invention is carried out stepwise.

In Step (A), an α-chloro or α-bromo oxime is allowed to react with an aminoacetonitrile in a suitable solvent in the presence of an acid uptake agent, which agent neutralizes the hydrogen halide formed during the reaction. The α-chloro oxime compounds are preferred for use in this reaction because of the ready availability of nitrosyl chloride for use in their preparation. Only the α-chloro oximes will therefore be used to illustrate the teachings set forth in this specification. However, the α-bromo oximes would be expected to react in the same manner as the α-chloro oximes do in the preparation of the hydroxyimino-substituted aminoacetonitrile compounds. Suitable solvents are those inert to the reactants and operating conditions employed in the reaction, and include chloroform, methylene chloride, tetrahydrofuran, benzene, and chlorobenzene. The solvent of choice is selected from the group consisting of chloroform and methylene chloride. Suitable acid uptake agents include the aminoacetonitrile itself, as well as those non-nucleophilic bases which are more basic than the aminoacetonitrile. Such bases include tertiary amine bases such as triethylamine, trimethylamine, tributylamine, and N-methylmorpholine, with triethylamine being the agent of choice.

Thus, the aminoacetonitrile, either as the free base, or as an acid addition salt, e.g., the hydrochloric acid addition salt, or a like acid addition salt, is suspended in a solvent selected from those solvents listed hereinbefore. When the aminoacetonitrile is used in the form of its acid addition salt, two moles of an acid uptake agent are added to the suspension. One mole of acid uptake agent serves to prepare the aminoacetonitrile free base, and the second mole of acid uptake agent serves to neutralize the hydrogen halide formed during the reaction between the aminoacetonitrile and the α-chloro oxime. To the mixture of aminoacetonitrile free base, solvent, and acid uptake agent, cooled to a temperature between about −5° to about 25° C., there is added, with stirring, a solution of the α-chloro oxime in the same solvent, at such a rate as to make possible the ready maintenance of the temperature of the mixture in the range of from about −5° to about 25° C. At the completion of the addition, the reaction mixture is allowed to warm to room temperature with continued stirring over a period of about 1 hour.

The product from Step (A), the hydroxyimino-substituted aminoacetonitrile, can be handled in a number of different ways in readying it for cyclization by the chosen acid.

Thus, the product of Step (A) can be separated by removing the solvent in vacuo, and the crude product, the hydroxyimino-substituted aminoacetonitrile, can be used as is in the cyclization reaction.

Alternatively, the crude product of Step (A) remaining after removal of the solvent can be crystallized from a suitable solvent, for example, a mixture of hexane and a chlorinated hydrocarbon. The crystalline product is then utilized in the cyclization reaction.

In still another method, the crude product of Step (A) can be separated from its various impurities by preparation of a crystalline salt, for example, the p-toluenesulfonate salt of the hydroxyimino-substituted aminoacetonitrile.

The preferred method for separating the hydroxyimino-substituted aminoacetonitrile is described hereinafter as Step (B), and Step (B) is conducted in the following manner.

The reaction mixture (from Step (A)) is washed successively with portions of water and saturated aqueous sodium chloride solution. The organic layer is separated and dried over a suitable drying agent, or by filtering through a filterpad of the drying agent.

The dried solution of the crude hydroxyimino-substituted aminoacetonitrile is reduced to about one-half its volume by evaporating the solvent. There is added to the reduced volume of solution with stirring, an amount of a hydrocarbon selected from the group consisting of hexane, pentane, heptane, and cyclohexane, sufficient to restore the original volume. The mixture is stirred at about room temperature, during which operation the product crystallizes, and is filtered off. This method of separation provides the hydroxyimino-substituted aminoacetonitrile remarkably free from undesirable impurities which may be carried over from the steps for preparing the α-chloro oxime, and provides product particularly well-suited for cyclization with a suitable acid in the present novel preparation of substituted 2-aminopyrazine compounds.

It is possible to combine the preparation of the α-chloro oxime with Step (A) of the abovedescribed novel method for the preparation of 2-aminopyrazines. In so doing, the reaction between the nitrosyl chloride and the substituted styrene in the presence of hydrogen chloride to yield the α-chloro oxime is carried out in the same solvent to be utilized in the later preparation of the hydroxyimino-substituted aminoacetonitrile, i.e., chloroform, methylene chloride, tetrahydrofuran, benzene, or chlorobenzene. The reaction product mixture is worked up by purging the excess nitrosyl chloride and hydrogen chloride from the reaction mixture with nitrogen, followed by washing the solution containing the α-chloro oxime with water. The washed solution of the α-chloro oxime is then used directly in the reaction with the aminoacetonitrile to prepare the hydroxyimino-substituted aminoacetonitrile.

It should be noted that if the phenyl group of the α-chloro oxime bears a halo or $C_1$–$C_3$ alkyl ($R^2$=halo or $C_1$–$C_3$ alkyl) in an ortho position, the yield of the subsequent hydroxyimino-substituted aminoacetonitrile of Formula (II), supra, can be appreciably lower due to steric factors.

In Step (C) of this novel method of preparing substituted 2-aminopyrazines, the product separated in Step (B), a hydroxyimino-substituted aminoacetonitrile of Formula II, is added slowly, with stirring, to a volume of a suitable acid selected from the group consisting of polyphosphoric acid, 85% phosphoric acid, and a mixture of phosphoric acid with phosphorus pentoxide. The addition can be accomplished at room temperature, or, if desired, the acid selected for use in the cyclization reaction can be warmed somewhat if it appears such warming will facilitate mixing the reactants.

The preferred acid for bringing about the cyclization of the hydroxyimino-substituted aminoacetonitriles is a phosphorus-containing acid. The phosphorus-containing acid to be used in the novel cyclization step is selected from the group of acids consisting of the polyphosphoric acid (or PPA) which is commercially available (also known as 115% phosphoric acid), 85% phosphoric acid, and a mixture of phosphoric acid and phosphorus pentoxide.

As is well known to those skilled in the art, the commercially available polyphosphoric acid contains phosphorus pentoxide in a polymerized form. For discussion of polyphosphoric acid, see F. Uhlig and H. R. Snyder, "Polyphosphoric Acid As A Reagent in Organic Chemistry", *Advances In Organic Chemistry* Vol. I, page 35 (Interscience Publishers, New York, 1960). A mixture, prepared as needed, of phosphorus pentoxide and orthophosphoric acid, such mixture containing a ratio of phosphorus pentoxide to orthophosphoric acid similar to that present in the commercially available polyphosphoric acid, is also suitable for use in the cyclization reaction, and will operate satisfactorily to bring about the desired cyclization. Such a mixture desirably contains at least enough phosphorus pentoxide to react completely with all the water produced in the cyclization reaction. The acid of choice for use in the novel cyclization step is the commercially available polyphosphoric acid, the preference being based on the convenience of obtaining the acid.

The cyclization reaction does proceed to some extent under conditions where a strong acid such as hydrochloric, sulfuric or p-toluenesulfonic acid is used in a solvent, or a mixture of methanesulfonic acid and phosphorus pentoxide is used as the cyclizing agent, but the yields are poor.

The time for the cyclization reaction to proceed to substantial completion depends on the temperature. Thus, heating the reaction mixture at a higher temperature will bring about cyclization more rapidly, but longer periods of heating will not increase the yield. Heating above about 50° C. is preferable, since such heating makes the polyphosphoric acid easier to stir and makes possible a more thorough and complete blending of the hydroxyimino-substituted aminoacetonitrile with the polyphosphoric acid.

In carrying out the addition, the hydroxyimino-substituted aminoacetonitrile is added portionwise, with stirring, to the polyphosphoric acid (PPA) at room temperature, or somewhat above, with time being allowed for the exothermic reaction which occurs to subside. While not specifically necessary, preheating warms the PPA sufficiently to permit the efficient stirring and blending of the hydroxyimino-substituted aminoacetonitrile and the PPA. Control of the exotherm is aided by the portionwise addition of the hydroxyimino-substituted aminoacetonitrile and also by having the PPA preheated to a temperature of from about 80°–85° C. The portionwise addition of the hydroxyimino-substituted aminoacetonitrile to the preheated PPA allows the cyclization reaction to proceed at such a rate that the temperature of the reaction mixture is readily maintained at about 80°–85° C., due to the heat produced by the reaction.

The amount of PPA required for the cyclization reaction depends on the amount of hydroxyiminosubstituted aminoacetonitrile used in the reaction. This relationship can be expressed as a ratio of PPA:hydroxyimino-substituted aminoacetonitrile, which ratio preferably may be varied from about 5:1 to about 15:1, by weight, suitably from about 5:1 to about 10:1, by weight. While a larger amount of PPA in the reaction makes stirring easier, and does not affect the reaction mechanism or the yield of desired product, it does make the work-up of the reaction less easy, since there is more PPA to be neutralized during the work-up. The viscosity of the reaction mixture is inversely proportional to the temperature and the concentration of the hydroxyimino-substituted aminoacetonitrile in the PPA, and the choice of ratio, in practice, will be made on consideration of the capability of the reaction equipment to mix and stir viscous mixtures.

After all the hydroxyimino-substituted aminoacetonitrile is added, heating and stirring of the mixture are continued at a temperature and for a period of time sufficient to bring about substantial completion of the cyclization reaction to form the substituted 2-aminopyrazine. Thus, after the addition is complete, the heating and stirring are continued for from about ½ hour to about 2 hours, suitably for about 1 hour at a suitable reaction temperature. The reaction temperature can vary somewhat, suitably within the range of from about 50° to about 140° C., preferably from about 80° to about 120° C., optimally from about 80° to about 95° C.

The reaction mixture is ordinarily worked up by pouring it into water preferably made slightly basic with, for example, ammonia, stirring the water continuously during the addition of the reaction mixture. Alternatively, water may be carefully poured into the reaction vessel with stirring and cooling. The pH of the aqueous mixture thus obtained is adjusted to about pH 8–9, by adding base to the mixture. Suitable bases for this purpose include ammonium hydroxide, potassium hydroxide, and sodium hydroxide. The basic aqueous mixture is then stirred for a period of time and filtered to separate the desired substituted 2-aminopyrazine as a solid. In the laboratory, about a 4-hour period of stirring prior to filtration is a sufficient period of time to produce good results. The high concentration of phosphate salt in the mixture appears to have a salting-out effect, and aids in the precipitation of the desired product from the mixture.

Although the isolation of the substituted 2-aminopyrazine by filtration from the basic aqueous mixture has been described above, the desired product can also be isolated by other methods known to those skilled in the art, such as solvent extraction. The specific conditions for the isolation of the product by filtration or by solvent extraction will be dictated in practice by the physical properties of the particular substituted 2-aminopyrazine.

The preparation of the α-chloro oximes used as starting materials for preparing the hydroxyimino-substituted aminoacetonitriles is known in the art, and can be described as follows. A styrene derivative, for example β-methylstyrene, is dissolved in an inert solvent such as methylene chloride or chloroform, the solution cooled to a temperature of about 0° to −5° C., and the solution saturated with anhydrous hydrogen chloride. The flow of anhydrous hydrogen chloride is then continued while nitrosyl chloride is added to the solution. Stirring and introduction of anhydrous hydrogen chloride are both continued while the reaction mixture is allowed to warm to room temperature over a period of about ½ hour. The reaction mixture is then purged with nitrogen for about ½ hour to remove the excess hydrogen chloride and nitrosyl chloride. The reaction mixture is washed successively with water and aqueous sodium chloride solution, and dried over a suitable drying agent, for example, anhydrous sodium sulfate. The drying agent is filtered off and the filtrate concentrated in vacuo to yield an oil, which is the crude α-chloro oxime. Since α-chloro oximes are thermally unstable, excessive heating is to be avoided during the work-up. The oil is taken up in hexane, and the crystalline product which forms is filtered off. In the instant illustration, the product is identified as 1-chloro-1-phenyl-2-propanone oxime, having a melting point of about 90°–92° C. The other α-chloro oximes used herein are prepared by the same general procedure. The same general procedure, but using nitrosyl bromide and hydrogen bromide, may presumably be used to prepare the corresponding α-bromo oximes.

It is also possible to start with the appropriately substituted styrene and to proceed to the hydroxyimino-substituted aminoacetonitrile without isolation of or crystallization of the intermediate α-chloro oxime. Thus, the preparation of the α-chloro oxime is carried out as previously described, using the solvent of choice for the preparation of the hydroxyimino-substituted amino-acetonitrile. At the completion of the reaction between the substituted styrene and the nitrosyl chloride to yield the α-chloro oxime, the solution containing the crude α-chloro oxime is washed with water and the organic layer containing the crude α-chloro oxime is used directly and added to the mixture of aminoacetonitrile (either as the free base or as an acid addition salt, e.g., the hydrochloride salt), acid uptake agent, and solvent, the solvent being the same one employed in the preparation of the α-chloro oxime. The reaction is allowed to proceed for the requisite period of time to bring about substantially complete formation of the hydroxy-imino-substituted aminoacetonitrile. The product is isolated in the same manner as previously described.

With the exception of three compounds, the styrene compounds herein utilized for preparing the α-chloro oximes are known and their preparations are published in the prior art. The compounds not previously known are synthesized following well-known published procedures. Thus, 2-bromobenzaldehyde is allowed to react with a Grignard reagent, ethyl magnesium bromide in anhydrous ether, to yield 1-(2-bromophenyl)propanol. This propanol derivative is then dehydrated by refluxing it in toluene in the presence of p-toluenesulfonic acid catalyst to yield the desired 1-bromo-2-(1-propenyl)benzene. Another previously unknown substituted styrene, namely, 1,2-dichloro-4-(1-propenyl)benzene is prepared by the same general procedure from 3,4-dichlorobenzaldehyde and ethyl magnesium bromide, followed by dehydration of the intermediate substituted propanol.

The third styrene compound not previously known is 1-ethyl-4-(1-propenyl)benzene, and it too is prepared by procedures appearing in the literature. Thus, the condensation of ethylbenzene with propionyl chloride in the presence of aluminum chloride in a Friedel-Crafts reaction yields the known 4-ethylpropiophenone. This ketone is readily reduced using sodium borohydride to yield 1-(4-ethylphenyl)propanol, which is dehydrated by heating with potassium bisulfate, to yield the desired 1-ethyl-4-(1-propenyl)benzene.

The following are descriptions of the preparation of the three new substituted styrenes, and several intermediate α-chloro oximes usable in the novel method of this invention.

PREPARATION 1

1-Bromo-2-(1-propenyl)benzene

This compound was prepared stepwise.

Step 1.

A solution of 34.46 g. (0.186 moles) of 2-bromobenzaldehyde in 93 ml. of anhydrous ethyl ether was added over a period of 15 minutes to a mixture of 75.6 ml. of a 2.71 M solution of ethyl magnesium bromide in 186 ml. of anhydrous ether held at a temperature of about 15° C. The reaction mixture was allowed to stand overnight at room temperature, after which it was cooled while 32 ml. of an aqueous 25% ammonium chloride solution was added. The ether was decanted from the solid residue, which residue was washed with ether and the washings added to the original ether layer. The combined ether layers were dried over anhydrous magnesium sulfate. The drying agent was filtered off and the ether solution concentrated to yield a light yellow oil weighing 32.21 g. The oil was identified by NMR spectrum as 1-(2-bromophenyl)propanol.

Step 2.

A mixture of 25 g. (0.116 moles) of 1-(2-bromophenyl)propanol (prepared in Step 1), 80 ml. of toluene, and 1.0 g. of p-toluenesulfonic acid was refluxed under a Dean-Stark water separator for about 4 hours. The reaction mixture was then cooled, stirred for about 15 minutes with 20 ml. of 5 N aqueous sodium hydroxide solution, and the aqueous layer separated and discarded. The organic layer was washed with 3 portions of water and dried over anhydrous sodium sulfate. The drying agent was filtered off and the filtrate concentrated to yield crude product weighing 20.65 g. A portion weighing 19.5 g. was distilled to yield product having a boiling point of about 82°–85° C./3–4 mm., and identified by NMR spectrum as 1-bromo-2-(1-propenyl)benzene.

Following the same general procedures, and using appropriate starting materials, the following compound was prepared and identified.

PREPARATION 2

1,2-Dichloro-4-(1-propenyl)benzene

Step 1.

1-(3,4-Dichlorophenyl)propanol, as a dark yellow liquid, weighing 40.02 g., from 36.0 g. (0.20 mole) of 3,4-dichlorobenzaldehyde and 77.6 ml. of a 2.71 M solution of ethyl magnesium bromide.

Step 2

1,2-Dichloro-4-(1-propenyl)benzene, as a dark amber liquid, weighing 29.61 g., from 40.02 g. (0.195 moles) of 1-(3,4-dichlorophenyl)propanol, 100 ml. of toluene, and 1.0 g. p-toluenesulfonic acid. Identified by NMR spectrum.

PREPARATION 3

1-Ethyl-4-(1-propenyl)benzene

This compound was prepared stepwise.

Step 1.

To a solution of 19 g. (0.117 moles) of 4-ethylpropiophenone [prepared by the procedure of *Kindler and Li, Ber.* 74, 321 (1941)] in 30 ml. of ethanol, there was added dropwise a solution of 1.76 g. of sodium hydroxide and 1.4 g. of sodium borohydride in 17.6 ml. of water. As addition proceeded, an exothermic reaction occurred and the temperature rose to about 35° C., and then, as addition continued, to about 75° C., after which the reaction temperature dropped to about room temperature. The reaction mixture was stirred at room temperature for about 1 hour. It then was stirred and heated at about 70°–75° C. for about two hours, after which the heating and stirring was continued overnight at this temperature. The reaction mixture was allowed to cool. There was added a solution of 0.6 g. of sodium hydroxide and 0.47 g. of sodium borohydride in 6 ml. of water, and the reaction mixture again heated and stirred at about 70°–75° C. overnight.

The reaction mixture was cooled, diluted with water, and the organic layer separated. The aqueous layer was extracted with three portions of ether, after which the aqueous layer was discarded. The ether extracts were combined with the original organic layer, and washed successively with water, aqueous sodium bicarbonate solution, saturated aqueous sodium chloride solution, and then dried over anhydrous magnesium sulfate.

The drying agent was filtered off, the solvent evaporated in vacuo, and the residual oil distilled to yield product having a boiling point of about 173°–176° C./100 mm. The product was identified by NMR spectrum as 1-(4-ethylphenyl)propanol.

Step 2.

In a 50 ml. 3-neck round bottom flask equipped with a non-pressure-equalizing addition funnel, a jacketed, variable take-off distillation head, and a magnetic stirring bar, was placed 15 g. (0.11 moles) of crystalline potassium bisulfate. The pressure in the flask was reduced to about 90 mm. and, while the potassium bisulfate was magnetically stirred, the flask and contents were heated in an oil bath to a temperature of about 220°–230° C., and there was added dropwise 60 g. (0.365 moles) of 1-(4-ethylphenyl)propanol to the potassium bisulfate in the flask. During the addition, some material having a boiling point of about 125°–135° C./90 mm. distilled out of the reaction mixture in the flask. After the addition was complete, the distillation was continued at the reduced pressure of 90 mm. until distillation ceased. The pressure was then reduced to 50 mm. and distillation continued at that pressure until distillation again ceased. Ether was added to the distillate, the aqueous layer separated and discarded, and the ether layer dried over anhydrous magnesium sulfate. The drying agent was filtered off and the ether removed in vacuo to leave 48.3 g. of a clear oil. The oil was identified by NMR spectrum as 1-ethyl-4-(1-propenyl)benzene.

PREPARATION 4

1-Chloro-1-phenyl-2-propanone oxime

A solution of 34.65 g. (0.294 moles) of $\beta$-methylstyrene in 300 ml. of chloroform was stirred and cooled to a temperature of about 0° to −3° C., and while this temperature was maintained, the solution was saturated with anhydrous hydrogen chloride. To the solution there was added 20.2 g. (0.307 moles) of nitrosyl chloride with a simultaneous flow of anhydrous hydrogen chloride sufficient to give an acid test at the vent from the reaction flask. The addition of the nitrosyl chloride took about 50 minutes. The reaction mixture was allowed to stir and warm to room temperature over a period of about 30 minutes with a continued flow of anhydrous hydrogen chloride at about 60 ml. per minute. At the end of that time the excess gases were purged from the system using dry nitrogen, the purge being carried out for about 30 minutes. The reaction mixture was washed twice with 150 ml. portions of water, followed by a wash with an aqueous solution of sodium chloride. The organic layer was dried over anhydrous sodium sulfate for about 10 minutes and the drying agent was filtered off. The filtrate was concentrated at reduced pressure to yield an oil which was stirred while 50 ml. of hexane was added. Crystals quickly formed while the mixture was stirred at room temperature for about 30 minutes. After standing in the refrigerator over the weekend the cold mixture was again stirred for about 15 minutes, filtered, and the solid on the filter washed with 50 ml. of cold hexane. There was obtained 38.12 g. (70.7% yield) of a product having a melting point of about 90°–92° C., and identified as 1-chloro-1-phenyl-2-propanone oxime.

| Analyses calculated for $C_9H_{10}ClNO$: | | |
|---|---|---|
| | Theoretical | Found |
| C | 58.87 | 59.03 |
| H | 5.49 | 5.20 |
| N | 7.63 | 7.69 |
| Cl | 19.31 | 19.30 |

Following the general procedure of Preparation 4, additional $\alpha$-chloro oximes were prepared and identified as follows.

PREPARATION 5

1-(2-Bromophenyl)-1-chloro-2-propanone oxime, as an oil, weighing 8.97 g., from 8.2 g. (0.042 moles) of 1-bromo-2-(1-propenyl)benzene and 3.0 g. (0.046 moles) of nitrosyl chloride. An analytical sample recrystallized from benzene/hexane had a melting point of about 121°–122.5° C.

Analyses calcualted for C₉H₉BrClNO:

|   | Theoretical | Found |
|---|---|---|
| C | 41.18 | 40.97 |
| H | 3.46 | 3.23 |
| Br | 30.44 | 30.63 |
| Cl | 13.50 | 13.26 |
| N | 5.34 | 5.37 |

PREPARATION 6

1-(3-Bromophenyl)-1-chloro-2-propanone oxime, as an oil, weighing 16.47 g., from 12.5 g. (0.063 moles) of 1-bromo-3-(1-propenyl)benzene and 4.36 g. (0.066 moles) of nitrosyl chloride. The product was identified by its NMR spectrum.

PREPARATION 7

1-(4-Bromophenyl)-1-chloro-2-propanone oxime, having a melting point of about 99°–100° C., weighing 157.7 g., from 232.6 g. (purity 86%) (1.01 moles) of 1-bromo-4-(1-propenyl)benzene and 66.5 g. (1.01 moles) of nitrosyl chloride.

Analyses calculated for C₉H₉BrClNO:

|   | Theoretical | Found |
|---|---|---|
| C | 41.18 | 41.01 |
| H | 3.46 | 3.43 |
| Br | 30.44 | 30.56 |
| Cl | 13.50 | 13.65 |
| N | 5.34 | 5.20 |

PREPARATION 8

1-(4-Bromophenyl)-1-chloro-2-butanone oxime, weighing 5.27 g., from 12.5 g. (0.059 moles) of 1-bromo-4-(1-butenyl)benzene and 3.88 g. (0.059 moles) of nitrosyl chloride. The analytical sample had a melting point of about 98°–99° C.

Analyses calculated for C₁₀H₁₁BrClNO:

|   | Theoretical | Found |
|---|---|---|
| C | 43.43 | 43.63 |
| H | 4.01 | 3.97 |
| Br | 28.89 | 28.77 |
| Cl | 12.82 | 12.76 |
| N | 5.06 | 4.98 |

PREPARATION 9

1-(2,4-Dimethylphenyl)-1-chloro-2-propanone oxime, having a melting point of about 104°–106° C., and weighing 4.79 g., from 6.0 g. (0.04 moles) of 2,4-dimethyl-1-propenylbenzene and 2.96 g. (0.045 moles) of nitrosyl chloride. Identified by NMR spectrum.

PREPARATION 10

1-Chloro-1-(3-trifluoromethylphenyl)-2-propanone oxime, as a green oil weighing 18.87 g., from 15 g. (0.0806 moles) of 1-trifluoromethyl-3-(1-propenyl)benzene and 9.24 g. (0.14 moles) of nitrosyl chloride. Identified by NMR spectrum.

PREPARATION 11

1-Chloro-1-(4-chlorophenyl)-2-propanone oxime, having a melting point of about 80°–81° C., and weighing 9.09 g., from 15.25 g. (0.1 mole) of 1-chloro-4-(1-propenyl)benzene and 6.88 g. (0.10 mole) of nitrosyl chloride. Identified by IR and NMR spectra.

PREPARATION 12

1-(3,4-Dichlorophenyl)-1-chloro-2-propanone oxime, as an oil, weighing 21.1 g., from 18.7 g. (0.10 mole) of 1,2-dichloro-4-(1-propenyl)benzene and 6.88 g. (0.10 mole) of nitrosyl chloride. The product was identified by its NMR spectrum.

PREPARATION 13

1-(4-Ethylphenyl)-1-chloro-2-propanone oxime, having a melting point of about 39°–40° C., and weighing 21 g., from 22 g. (0.15 moles) of 1-ethyl-4-(1-propenyl)benzene and 9.9 g. (0.15 moles) of nitrosyl chloride. The product was identified by its NMR spectrum.

The following preparation illustrates the synthesis of a hydroxyimino-substituted aminoacetonitrile starting with a substituted styrene and continuing via the resulting α-chloro oxime, without separation and purification of that intermediate α-chloro oxime, but keeping said oxime in solution and adding the solution to a mixture of an aminoacetonitrile (or aminoacetonitrile acid addition salt), an acid uptake agent, and a suitable solvent, all as has been described hereinbefore.

PREPARATION 14

[[1-(4-Bromophenyl)-2-(hydroxyimino)propyl-]amino]acetonitrile

A solution of 27.7 kg. of 1-bromo-4-(1-propenyl)benzene (purity, 90%) in 110 l. methylene chloride was cooled to about 0° C. and saturated with hydrogen chloride. Nitrosyl chloride (8.74 kg.) was bubbled into the mixture at such a rate that the temperature was maintained below about 10° C. Addition of hydrogen chloride was continued concurrently with the nitrosyl chloride addition at such a rate that saturation of the mixture with hydrogen chloride was maintained. When addition of nitrosyl chloride was complete the mixture was stirred for an additional 15 minutes under hydrogen chloride saturation, then purged with nitrogen to remove excess nitrosyl chloride and hydrogen chloride. The mixture was washed with three 60 l. portions of water, and the layers separated. The methylene chloride layer, containing the α-chloro oxime product, was dripped slowly into a second reaction vessel containing a mixture of 11.6 kg. of aminoacetonitrile hydrochloride, 25.2 kg. of triethylamine, and 120 l. of methylene chloride cooled to about 10° C., so that the reaction temperature was maintained below 20° C. The mixture was allowed to warm to about 25° C. over about 2 hrs., then washed with three 60 l. portions of water. The methylene chloride layer was carefully concentrated under vacuum to a volume of about 100 l. The temperature of the solution was adjusted to about 40° C. and 100 l. of hexane, warmed to a temperature of about 40° C., was added with stirring. The product crystallized as the mixture was slowly cooled and stirred at room temperature overnight. The mixture was cooled briefly to about 0°–5° C., then filtered and the crystals washed with hexane. There was thus obtained 18.7 kg. of [[1-(4-bromophenyl)-2-(hydroxyimino)propyl]amino]acetonitrile, having a m.p. of about 108°–110° C. The yield was calculated to be about (52.5% of theory based on the weight of 1-bromo-4-(1-propenyl)benzene used. The purity of the product was estimated to be about 98% by a gas chromatographic method.

The novel method of this invention is broadly demonstrated by the following operating examples, but the invention is not to be considered as limited by the examples.

EXAMPLE 1

2-Amino-6-methyl-5-phenylpyrazine

The synthesis of this substituted 2-aminopyrazine is carried out stepwise.

Step A

To a suspension of 11.56 g. (0.125 moles) of aminoacetonitrile hydrochloride in 90 ml. of chloroform, stirred under a nitrogen atmosphere and cooled to about 0° C. in an ice-bath, was added 22.73 g. (0.225 moles) of triethylamine. While the temperature was maintained at about 0° C., there was added to the resulting mixture a solution of 18.35 g. (0.10 moles) of 1-chloro-1-phenyl-2-propanone oxime in 85 ml. of chloroform over a period of about 2 hours. The reaction mixture was then allowed to warm to room temperature over a period of about 1 hour.

Step B

The reaction mixture was washed twice with 100 ml. portions of water, and one 100 ml. portion of saturated brine, and dried by filtration through a pad of anhydrous sodium sulfate. The filtrate was reduced to about ½ its volume by concentrating it under reduced pressure, and sufficient hexane was added thereto to restore the original volume. The resulting mixture was stirred at about room temperature, allowing the product to crystallize. After standing in the refrigerator overnight, the mixture was filtered and the crystals remaining on the filter were washed with 75 ml. of cold hexane. In this manner there was obtained 13.22 g. (65% yield) of product identified as [[2-(hydroxyimino)-1-(phenyl)-propyl]amino]acetonitrile, having a melting point of about 94.5°–96.5° C. A sample recrystallized from ethanol had a melting point of about 96°–97.5° C. The product was identified by elemental analyses, NMR and mass spectra.

Analyses calculated for $C_{11}H_{13}N_3O$:

|   | Theoretical | Found |
|---|---|---|
| C | 65.01 | 65.18 |
| H | 6.45 | 6.55 |
| N | 20.68 | 20.39 |

Step C

A 10 g. portion of the hydroxyimino-substituted acetonitrile prepared in Step B, supra, was slowly added with stirring over a period of about ½ hour to 100 g. of polyphosphoric acid preheated to a temperature of about 80°–85° C. The rate of addition was adjusted so that the temperature of the mixture was maintained in the range of from about 80° to 90° C. When addition was complete, the mixture was heated to about 90°–110° C. for about 1 hour, then poured into a mixture of 320 ml. of water and 13 ml. of concentrated ammonium hydroxide. The resulting suspension was cooled to about 30° C., and 110 ml. of concentrated ammonium hydroxide added to adjust the mixture to about pH 8–9. The mixture was stirred for about 4 hours, filtered, and the solid which was collected on the filter washed with water and dried in vacuo at about 40° C. There was obtained product (a light tan solid) weighing 8.3 g. (91% yield), and identified as 2-amino-6-methyl-5-phenylpyrazine. A sample recrystallized from ethanol had a melting point of about 136.5°–138° C. The structure was confirmed by elemental analyses, NMR, UV, and mass spectra.

Analyses calculated for $C_{11}H_{11}N_3$:

|   | Theoretical | Found |
|---|---|---|
| C | 71.33 | 71.63 |
| H | 5.99 | 6.01 |
| N | 22.69 | 22.75 |

Following the general procedure of Steps A, B, and C of Example 1, additional substituted 2-aminopyrazines were prepared. The weights of reactants and products are recorded in the examples which follow.

EXAMPLE 2

2-Amino-5-(2-Bromophenyl)-6-Methylpyrazine

Step A and Step B

[[1-(2-Bromophenyl)-2-(hydroxyimino)propyl]amino]acetonitrile, weighing 1.25 g., from 5.0 g. (0.019 moles) of 1-(2-bromophenyl)-1-chloro-2-propanone oxime, 2.2 g. (0.024 moles) of aminoacetonitrile hydrochloride and 4.33 g. (0.043 moles) of triethylamine. The analytical sample had a melting point of about 139°–142° C.

Analyses calculated for $C_{11}H_{12}BrN_3O$:

|   | Theoretical | Found |
|---|---|---|
| C | 46.83 | 46.67 |
| H | 4.29 | 4.14 |
| N | 14.89 | 14.74 |
| Br | 28.32 | 28.56 |

Step C

2-Amino-5-(2-bromophenyl)-6-methylpyrazine, having a melting point of about 177°–179° C., and weighing 0.5 g., from 1.2 g. of [[1-(2-bromophenyl)-2-(hydroxyimino)propyl]amino]acetonitrile, prepared in Steps A and B, and 12 g. of polyphosphoric acid.

Analyses calculated for $C_{11}H_{10}N_3Br$:

|   | Theoretical | Found |
|---|---|---|
| C | 50.02 | 49.79 |
| H | 3.82 | 3.67 |
| N | 15.91 | 15.72 |

EXAMPLE 3

2-Amino-5-(3-Bromophenyl)-6-Methylpyrazine

Step A and Step B

[[1-(3-Bromophenyl)-2-(hydroxyimino)propyl-]amino]acetonitrile, as an oil, and weighing 5.4 g., from 5.0 g. (0.019 moles) of 1-(3-bromophenyl)-1-chloro-2-propanone oxime, 2.2 g. (0.024 moles) of aminoacetonitrile hydrochloride, and 4.33 g. (0.43 moles) of triethylamine. The analytical sample had a melting point of about 96°–98° C.

Analyses calculated for $C_{11}H_{12}BrN_3O$:

|   | Theoretical | Found |
|---|---|---|
| C | 46.83 | 46.72 |
| H | 4.29 | 4.10 |
| N | 14.89 | 14.67 |

Step C

2-Amino-5-(3-bromophenyl)-6-methylpyrazine, having a melting point of about 141°–145° C., and weighing 0.25 g., from 1.1 g. of [[1-(3-bromophenyl)-2-(hydroxyimino)propyl]amino]acetonitrile, from Steps A and B, and 11 g. of polyphosphoric acid. The product was identified by high resolution mass spectra.

High resolution MS: Calculated for $C_{11}H_{10}{}^{79}BrN_3$: 263.00586; Found: 263.00494.

EXAMPLE 4

2-Amino-5-(4-Bromophenyl)-6-Methylpyrazine

Step A and Step B

[[1-(4-Bromophenyl)-2-hydroxyimino)propyl-]amino]acetonitrile, weighing 44.8 g., from 45 g. (0.17 moles) of 1-(4-bromophenyl)-1-chloro-2-propanone oxime, 19.82 g. (0.21 moles) of aminoacetonitrile hydrochloride, and 38.96 g. (0.385 moles) of triethylamine. The analytical sample had a melting pont of about 111°–112° C.

Analyses calculated for $C_{11}H_{12}BrN_3O$:

|   | Theoretical | Found |
|---|---|---|
| C | 46.83 | 46.66 |
| H | 4.29 | 4.10 |
| N | 14.89 | 14.65 |

Step C

2-Amino-5-(4-bromophenyl)-6-methylpyrazine, weighing 25.4 g., from 28.2 g. of [[1-(4-bromophenyl)-2-(hydroxyimino)propyl]amino]acetonitrile, from Steps A and B, and 282 g. of polyphosphoric acid. The analytical sample had a melting point of about 191.5°–193° C.

Analyses calculated for $C_{11}H_{10}BrN_3$:

|   | Theoretical | Found |
|---|---|---|
| C | 50.02 | 50.06 |
| H | 3.82 | 4.03 |
| N | 15.91 | 15.81 |

EXAMPLE 5

2-Amino-5-(4-Bromophenyl)-6-Ethylpyrazine

Step A and Step B

[[1-(4-Bromophenyl)-2-(hydroxyimino)butyl-]amino]acetonitrile, weighing 3.12 g., from 4.0 g. (0.0145 moles) of 1-(4-bromophenyl)-1-chloro-2-butanone oxime, 1.67 g. (0.018 moles) of aminoacetonitrile hydrochloride, and 3.29 g. (0.033 moles) of triethylamine. The analytical sample had a melting point of about 118.5°–120° C.

Analyses calculated for $C_{12}H_{14}BrN_3O$:

|    | Theoretical | Found |
|----|---|---|
| C  | 48.67 | 48.58 |
| H  | 4.76 | 4.51 |
| N  | 14.19 | 13.93 |
| Br | 26.98 | 27.17 |

Step C

2-Amino-5-(4-bromophenyl)-6-ethylpyrazine, weighing 1.78 g., from 2.5 g. of [[1-(4-bromophenyl)-2-(hydroxyimino)butyl]amino]acetonitrile, from Steps A and B, and 25 g. of polyphosphoric acid. The analytical sample had a melting point of about 204°–206° C.

Analyses calculated for $C_{12}H_{12}BrN_3$:

|    | Theoretical | Found |
|----|---|---|
| C  | 51.82 | 51.60 |
| H  | 4.35 | 4.25 |
| N  | 15.11 | 14.84 |
| Br | 28.73 | 28.68 |

EXAMPLE 6

2-Amino-5-(2,4-Dimethylphenyl)-6-Methylpyrazine

Step A and Step B

[[1-(2,4-Dimethylphenyl)-2-(hydroxyimino)propyl-]amino]acetonitrile, having a melting point of about 133°–134° C., and weighing 2.51 g., from 4.0 g. (0.019 moles) of 1-chloro-1-(2,4-dimethylphenyl)-2-propanone oxime, 2.18 g. (0.024 moles) of aminoacetonitrile hydrochloride, and 4.29 g. (0.042 moles) of triethylamine.

Analyses calculated for $C_{13}H_{17}N_3O$:

|   | Theoretical | Found |
|---|---|---|
| C | 67.51 | 67.58 |
| H | 7.41 | 7.18 |
| N | 18.17 | 18.01 |

Step C

2-Amino-5-(2,4-dimethylphenyl)-6-methylpyrazine, having a melting point of about 159.5°–161.5° C., and weighing 1.84 g., from 2.0 g. of [[1-(2,4-dimethylphenyl)-2-(hydroxyimino)propyl]amino]acetonitrile, prepared in Steps A and B, and 20 g. of polyphosphoric acid. The substituted 2-aminopyrazine was characterized by preparation of the 2,6-dichlorobenzoylurea derivative, which had a melting point of about 236°–237° C.

Analyses calculated for $C_{21}H_{18}Cl_2N_4O_2$:

|   | Theoretical | Found |
|---|---|---|
| C | 58.74 | 58.49 |
| H | 4.19 | 4.08 |
| N | 13.05 | 12.75 |

EXAMPLE 7

2-Amino-6-Methyl-5-[3-(Trifluoromethyl)phenyl]pyrazine

Step A and Step B

[[2-(Hydroxyimino)-1-[3-(trifluoromethyl)phenyl]-propyl]amino]acetonitrile, having a melting point of about 101°–103° C., and weighing 1.5 g., from 15 g. (0.0596 moles) of 1-chloro-1-(3-trifluoromethylphenyl)-2-propanone oxime, 5.52 g. (0.0596 moles) of aminoacetonitrile hydrochloride, and 12.05 g. (0.1192 moles) of triethylamine.

Analyses calculated for $C_{12}H_{12}F_3N_3O$:

|   | Theoretical | Found |
|---|---|---|
| C | 53.14 | 53.11 |
| H | 4.46 | 4.37 |
| N | 15.49 | 15.25 |
| F | 21.01 | 21.23 |

Step C

2-Amino-6-methyl-5-[3-(trifluoromethyl)phenyl]pyrazine, weighing 0.66 g., from 1.0 g. of [[2-(hydroxyimino)-1-[3-trifluoromethyl)phenyl]propyl]amino]acetonitrile of Steps A and B, and 10 g. of polyphosphoric acid. A sample recrystalized from ethanol had a melting point of about 154.5°–156.5° C. Identified by IR, NMR, UV, and mass spectra.

EXAMPLE 8

2-Amino-5-(4-Chlorophenyl)-6-Methylpyrazine

Step A and Step B

[[1-(4-Chlorophenyl)-2-(hydroxyimino)propyl]amino]acetonitrile, having a melting point of about 119.5°–121° C., and weighing 7.38 g., from 7.5 g. (0.034 moles) of 1-chloro-1-(4-chlorophenyl)-2-propanone oxime, 3.98 g. (0.043 moles) of aminoacetonitrile hydrochloride, and 7.82 g. (0.077 moles) of triethylamine.

Analyses calculated for $C_{11}H_{12}ClN_3O$:

|   | Theoretical | Found |
|---|---|---|
| C | 55.59 | 55.35 |
| H | 5.09 | 5.24 |
| Cl | 14.92 | 14.70 |
| N | 17.68 | 17.69 |

Step C

2-Amino-5-(4-chlorophenyl)-6-methylpyrazine, weighing 6.8 g., from 7.38 g. [[1-(4-chlorophenyl)-2-(hydroxyimino)propyl[amino]acetonitrile, prepared in Steps A and B, and 73.8 g. of polyphosphoric acid. The analytical sample had a melting point of about 191°–193.5° C.

Analyses calculated for $C_{11}H_{10}ClN_3$:

|   | Theoretical | Found |
|---|---|---|
| C | 60.14 | 59.89 |
| H | 4.59 | 4.62 |
| Cl | 16.14 | 16.17 |

EXAMPLE 9

2-Amino-5-(3,4-Dichlorophenyl)-6-Methylpyrazine

Step A and Step B

[[1-(3,4-Dichlorophenyl)-2-(hydroxyimino)propyl]amino]acetonitrile, weighing 1.82 g., from 10 g. (0.04 moles) of crude 1-chloro-1-(3,4-dichlorophenyl)-2-propanone oxime, 4.58 g. (0.049 moles) of aminoacetonitrile hydrochloride, and 9.0 g. (0.089 moles) of triethylamine. The analytical sample had a melting point of about 106.5°–107.5° C. Identified by IR, NMR and mass spectra. High resolution MS: calculated for $C_{11}H_{11}{}^{35}Cl_2N_3O$: 271.02791; found: 271.02807.

Step C

2-Amino-5-(3,4-dichlorophenyl)-6-methylpyrazine, weighing 0.82 g., from 1.0 g. of [[1-3,4-dichlorphenyl)-2-(hydroxyimino)phenyl)propyl]amino]acetonitrile, prepared in Steps A and B, and 10 g. of polyphosphoric acid. Recrystallization from ethanol gave product having a melting point of about 178°–180° C. Identified by high resolution mass spectra. High resolution MS: calculated for $C_{11}H_9{}^{35}Cl_2N_3$: 253.01734; found: 253.01647.

EXAMPLE 10

2-Amino-5-(4-Ethylphenyl)-6-Methylpyrazine

Step A and Step B

[[1-(4-Ethylphenyl)-2-(hydroxyimino)propyl]amino]acetonitrile, having a melting point of about 83°–85° C., and weighing 13.6 g., from 21.2 g. (0.10 moles) of 1-chloro-1-(4-ethylphenyl)-2-propanone oxime, 11.6 g. (0.125 moles) of aminoacetonitrile hydrochloride, and 25.2 g. (0.25 moles) of triethylamine. The product was identified by its NMR spectrum.

STEP C

2-Amino-5-(4-ethylphenyl)-6-methylpyrazine, having a melting point of about 148°–154° C., and weighing 4.05 g., from 7.5 g. of [[1-(4-ethylphenyl)-2-(hydroxyimino)propyl]amino]acetonitrile, prepared in Steps A and B, and 103 g. of polyphosphoric acid. The product was identified by its NMR spectrum.

The following Example illustrates the use of a greater ratio of polyphosphoric acid to the hydroxyimino-substituted aminoacetonitrile in the cyclization reaction.

EXAMPLE 11

2-Amino-6-Methyl-5-Phenylpyrazine

To 15 ml. (30.9 g.) of polyphosphoric acid (PPA), efficiently stirred at about ambient room temperature, there was added portionwise 1.0 g. of [[2-(hydroxyimino)-1-(phenyl)propyl]amino[acetonitrile over a period of about 5 minutes. No reaction appeared to occur and the solid hydroxyimino-substituted acetonitrile appeared to form a suspension in the PPA. The reaction mixture was gradually warmed to about 85° C., with continued stirring, and maintained at 85° C. for about 1.5 hours. Thin layer chromatography showed absence of starting material and presence of desired pyrazine compound. The reaction mixture was then poured into about 150 ml. of water, the aqueous mixture cooled with ice and neutralized by addition of concentrated ammonium hydroxide. The solid material which precipitated was filtered off and dried. The product weighed 0.55 g. (59% yield) and had a melting point of about 134°–135° C., and was identified as 2-amino-6-methyl-5-phenylpyrazine.

The above examples illustrate the preparation of substituted 2-aminopyrazines by reaction of an α-chloro oxime with an aminoacetonitrile in the presence of an acid uptake agent, separation of the intermediate hydroxyimino-substituted amino-acetonitrile, followed by cyclization thereof by heating in acid.

We claim:

1. A method for the preparation of 2-aminopyrazines of the formula

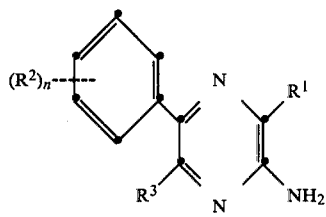

wherein
$R^1$ is hydrogen or $C_1$–$C_4$ alkyl;
$R^2$ is hydrogen, halo, $C_1$–$C_3$ alkyl, or trifluoromethyl;
n is 0, 1, or 2, with the proviso that when n=2, only one ortho position may be substituted; and
$R^3$ is $C_1$–$C_4$ alkyl,
which comprises (A) reacting an aminoacetonitrile of the formula

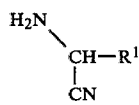

wherein $R^1$ has the same value as set forth hereinbefore, with an α-chloro or α-bromo oxime of the formula

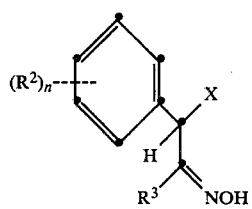

wherein X is chloro or bromo, and $R^2$, $R^3$, and n have the same values as set forth hereinbefore, in a solvent in the presence of an acid-uptake agent, to yield a hydroxyimino-substituted aminoacetonitrile of the following formula (II)

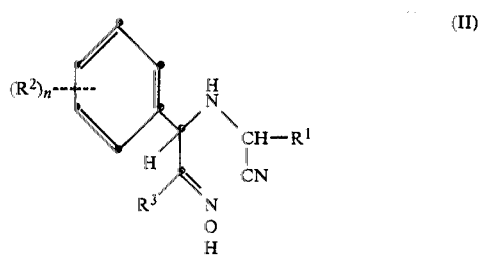

wherein $R^1$, $R^2$, $R^3$, and n have the same values as set forth hereinbefore; (B), separating the hydroxyimino-substituted aminoacetonitrile; and (C), heating the thus obtained hydroxyimino-substituted aminoacetonitrile in an acid selected from the group consisting of polyphosphoric acid, 85% phosphoric acid, and a mixture of phosphoric acid with phosphorus pentoxide, at a temperature of from about 50° to about 140° C., for from about ½ to about 4 hours, and isolating the product.

2. The method of claim 1 wherein the oxime employed in step A is an α-chloro oxime, as therein defined.

3. The method of claim 1 wherein the solvent for step A is chloroform.

4. The method of claim 1 wherein the solvent for step A is methylene chloride.

5. The method of claim 1 wherein step A is conducted at a temperature within the range of from about −5° to about 25° C.

6. The separation method of Step (B), claim 1, which comprises washing the reaction mixture from Step (A) successively with water and saturated aqueous sodium chloride, drying the mixture, concentrating the mixture to about ½ volume, adding thereto with stirring an amount of a hydrocarbon selected from the group consisting of hexane, pentane, heptane, and cyclohexane, sufficient to restore the original volume, allowing the mixture to stir at about room temperature, and separating the product.

7. The method of claim 5 wherein the hydrocarbon is hexane.

8. The method of Step (C), claim 1, which comprises heating a hydroxyimino-substituted aminoacetonitrile in an acid selected from the group consisting of polyphosphoric acid, 85% phosphoric acid, and a mixture of phosphoric acid with phosphorus pentoxide, at a temperature of from about 50° to about 140° C., for from about ½ to about 4 hours, and isolating the product.

9. The method of claim 7 conducted at a temperature within the range of from about 80° to about 120° C.

10. The method of claim 7 conducted at a temperature within the range of from about 80° to about 95° C.

11. The method of claim 7 wherein the acid is polyphosphoric acid.

12. The method of claim 7 wherein the ratio of polyphosphoric acid to hydroxy-imino substituted aminoacetonitrile is from about 5:1 to about 15:1.

* * * * *